United States Patent [19]
Bäckström et al.

[11] Patent Number: 5,658,878
[45] Date of Patent: Aug. 19, 1997

[54] THERAPEUTIC PREPARATION FOR INHALATION

[75] Inventors: Kjell Göran Erik Bäckström; Carl Magnus Olof Dahlbäck, both of Lund; Peter Edman, Bjärred; Ann Charlotte Birgit Johansson, Lund, all of Sweden

[73] Assignee: AB Astra, Sodertalje, Sweden

[21] Appl. No.: 471,488

[22] Filed: Jun. 6, 1995

Related U.S. Application Data

[62] Division of Ser. No. 265,372, Jun. 23, 1994, Pat. No. 5,518,998.

[30] Foreign Application Priority Data

| Jun. 24, 1993 | [SE] | Sweden | 9302198 |
| Feb. 4, 1994 | [SE] | Sweden | 9400370 |

[51] Int. Cl.$^6$ .................. C07K 14/62; A61K 38/28
[52] U.S. Cl. ........................... 514/3; 530/303
[58] Field of Search .................... 514/3; 530/303

[56] References Cited

U.S. PATENT DOCUMENTS

| 4,613,500 | 9/1986 | Suzuki et al. | 424/85.4 |
| 4,690,952 | 9/1987 | Kagatani et al. | 514/11 |
| 4,788,221 | 11/1988 | Kagatani et al. | 514/12 |
| 4,900,730 | 2/1990 | Miyauchi | 514/12 |
| 5,179,079 | 1/1993 | Hansen et al. | 514/4 |
| 5,202,129 | 4/1993 | Samejima et al. | 424/489 |
| 5,354,562 | 10/1994 | Platz et al. | 424/489 |
| 5,419,315 | 5/1995 | Rubsamen | 128/200 |
| 5,482,706 | 1/1996 | Igari et al. | 424/85.7 |
| 5,506,203 | 4/1996 | Bäckström et al. | 514/4 |

FOREIGN PATENT DOCUMENTS 0 360 340   3/1990   European Pat. Off. .

OTHER PUBLICATIONS

Olanoff et al., "Method to Enhance Intranasal Peptide Delivery," in Controlled–Release Technology Pharmaceutical Applications, Lee et al., American Chemical Society, 301–309, 1987.

*Primary Examiner*—Michael P. Woodward
*Assistant Examiner*—Benet Prickril
*Attorney, Agent, or Firm*—Fish & Richardson P.C.

[57] ABSTRACT

A therapeutic preparation for inhalation which comprises insulin and a substance which enhances the absorption of insulin in the lower respiratory tract, is provided in the form of a powder preparation suitable for inhalation.

32 Claims, 6 Drawing Sheets

Transport of mannitol across Caco-2 cell monolayer in presence of Na-caprate (10-16 mM)

A. Na-caprate
B. Na-caprate/insulin (1:3 w/w)

THERAPEUTIC PREPARATION FOR INHALATION

This is a divisional of application Ser. No. 08/265,372, filed Jun. 23, 1994, now U.S. Pat. No. 5,518,998.

This invention relates to a therapeutic preparation of insulin, which is suitable for inhalation.

BACKGROUND OF THE INVENTION

Insulin plays a central role in the regulation of carbohydrate, fat, and protein metabolism in the body. Diabetes mellitus (commonly referred to simply as diabetes) is a disease characterized by disregulation of metabolism, particularly glucose metabolism. In normal individuals, a rise in blood glucose levels (such as that which occurs immediately following eating) triggers the islet beta cells of the pancreas to secrete insulin, a peptide hormone, into the bloodstream. The insulin binds to insulin receptors located on a number of cell types, notably muscle cells, and thereby signals the cells to increase the rate of glucose uptake into the cells. As the blood glucose returns to normal pre-prandial levels, the amount of insulin in the blood also drops. In the absence of insulin, blood glucose levels would rise to dangerously high levels (a condition termed hyperglycemia), possibly resulting in death. Too much insulin causes abnormally low blood glucose levels (hypoglycemia), which is also dangerous and possibly fatal. In a normal individual, built-in feedback loops regulating the secretion of insulin and its clearance from the systemic circulation prevent both hyperglycemic and hypoglycemic conditions from occurring.

Diabetes mellitus is a disease affecting about 3% of the population of Sweden. Of these 3%, approximately 20% suffer from Type I diabetes, and the remainder from Type II diabetes.

Type I diabetes, or insulin-dependent diabetes mellitus (IDDM), usually begins in childhood. It is characterized by atrophy of the pancreatic beta cells, resulting in a decrease or cessation of insulin production, and leaving the patient dependent on exogenous insulin for survival.

The more common Type II diabetes, or non-insulin-dependent diabetes mellitus (NIDDM), generally occurs in patients older than 40 years. These patients may, at least initially, have normal or even high levels of insulin in their blood, but exhibit an abnormally low rate of cellular uptake of glucose in response to insulin. Although Type II diabetes often can be treated by controlling the patient's diet, administration of exogenous insulin to supplement that secreted by the patient's beta cells may also prove necessary.

Insulin cannot be orally administered in effective doses, since it is rapidly degraded by enzymes in the gastrointestinal tract and low pH in the stomach before it can reach the bloodstream. The standard method of administration is by subcutaneous injection of an isotonic solution of insulin, usually by the patient him/herself. The necessity for injection causes a great deal of inconvenience and discomfort to many sufferers, and local reactions can occur at the injection site. In addition there is an abnormal, non-physiological, plasma concentration profile for injected insulin. This abnormal plasma concentration profile is undesirable and increases the risk of side effects related to the long term treatment of diabetes.

Because of these disadvantages, there is a need for insulin in a form which is administrable other than by injection. In attempts to produce such different forms of insulin, various proposals have been made. For example, products for nasal, rectal and buccal administration have been suggested, with much effort being concentrated on products for nasal administration. Nasal administration is however problematic and permits only a very low bioavailability. Pulmonary delivery of systemically active drugs has gained increasing interest over the last years, and some investigations have included the pulmonary delivery of insulin. Most of these are concerned with solutions or suspensions for pulmonary delivery for example by nebulisers and pressurised metered dose inhalers, and all have met with limited success.

THE INVENTION

We have now found that insulin can be included in a dry powder preparation for inhalation also including a substance which enhances the absorption of insulin in the lung, from which preparation the insulin may be absorbed in a therapeutically acceptable rate and amount. By "enhances absorption" is meant that the amount of insulin absorbed into the systemic circulation in the presence of the enhancer is higher than the amount absorbed in the absence of enhancer.

According to this invention therefore, there is provided a therapeutic preparation comprising active compounds (A) insulin, and (B) a substance which enhances the absorption of insulin in the lower respiratory tract, which preparation is in the form of a dry powder suitable for inhalation in which at least 50% of the total mass of active compounds consists of (a) primary particles having a diameter of less than about 10 microns, for example between 0.01 and 10 microns and preferably between 1 and 6 microns, or (b) agglomerates of said particles.

The therapeutic preparation of the present invention may contain only the said active compounds or it may contain other substances, such as a pharmaceutically acceptable carrier. This carrier may largely consist of particles having a diameter of less than about 10 microns so that at least 50% of the resultant powder as a whole consists of optionally agglomerated primary particles having a diameter of less than about 10 microns; alternatively the carrier may largely consist of much bigger particles ("coarse particles"), so that an "ordered mixture" may be formed between the active compounds and the said carrier. In an ordered mixture, alternatively known as an interactive or adhesive mixture, fine drug particles (in this invention, the active compounds) are fairly evenly distributed over the surface of coarse excipient particles (in this invention, the pharmaceutically acceptable carrier). Preferably in such case the active compounds are not in the form of agglomerates prior to formation of the ordered mixture. The coarse particles may have a diameter of over 20 microns, such as over 60 microns. Above these lower limits, the diameter of the coarse particles is not of critical importance so various coarse particle sizes may be used, if desired according to the practical requirements of the particular formulation. There is no requirement for the coarse particles in the ordered mixture to be of the same size, but the coarse particles may advantageously be of similar size within the ordered mixture. Preferably, the coarse particles have a diameter of 60–800 microns.

In a particular embodiment therefore this invention provides a therapeutic preparation of insulin and a substance which enhances the absorption of insulin in the lower respiratory tract, which preparation is in the form of a dry powder preparation suitable for inhalation of which at least 50% by mass consists of (a) particles having a diameter of less than about 10 microns or (b) agglomerates of said particles; in a further particular embodiment, the invention provides a therapeutic preparation comprising insulin, a substance which enhances the absorption of insulin in the lower respiratory tract, and a pharmaceutically acceptable carrier, which preparation is in the form of a dry powder suitable for inhalation of which at least 50% by mass consists of (a) particles having a diameter of less than about 10 microns, or (b) agglomerates of said particles; and in a still further particular embodiment this invention provides a therapeutic preparation comprising active compounds (A) insulin and (B) a substance which enhances the absorption of insulin in the lower respiratory tract, wherein at least 50% of the total mass of active compounds (A) and (B) consists of particles having a diameter of less than about 10 microns, and a pharmaceutically acceptable carrier, which preparation is in the form of a dry powder preparation suitable for inhalation in which an ordered mixture may be formed between the active compounds and the pharmaceutically acceptable carrier.

Preferably at least 60% such as at least 70% or at least 80% and more preferably at least 90% of the total mass of active compounds (A) and (B) consists of particles having a diameter of less than about 10 microns, or of agglomerates of such particles, and, when the dry powder preparation comprises carrier other than when an ordered mixture is desired, preferably at least 60% such as at least 70% or at least 80% and more preferably at least 90% by mass of the total dry powder consists of particles having a diameter of less than about 10 microns, or of agglomerates of such particles.

While the dry powder for inhalation, whether with or without pharmaceutically acceptable carrier, may contain agglomerates of particles as indicated above, at the time of inhalation any agglomerates should be substantially deagglomerated yielding a powder of which at least 50% consists of particles having a diameter of up to 10 microns. The agglomerates can be the result of a controlled agglomeration process or they may simply be the result of the intimate contact of the powder particles. In either case it is essential that the agglomerates are capable of being de-agglomerated e.g. by mechanical means in the inhaler or otherwise, into the aforesaid particles. Agglomerates are in general preferably not formed in the ordered mixture. In the case of an ordered mixture, the active compounds should be released from the large particles preferably upon inhalation, either by mechanical means in the inhaler or simply by the action of inhalation, or by other means, the active compounds then being deposited in the lower respiratory tract and the carrier particles in the mouth.

DETAILED DESCRIPTION

Any biologically active form or derivative of insulin may be used in the present invention. For example bovine, porcine, or biosynthetic or semisynthetic human insulin, or a biologically active derivative of human insulin ("modified insulin"), for example having certain amino acid substitutions as taught by Brange et al in "Diabetes Care" 13:923, 1990, may be used. Modified insulins are developed in order to improve various properties, for example to improve stability or give an improved pharmokinetic profile (i.e. improved profile of absorption through the epithelial membranes). The insulin should have a low zinc content, since zinc lowers the solubility of insulin, probably reducing the absorption rate, and also because zinc may form undesirable insoluble precipitates with certain of the enhancer substances for use in the present invention. In addition the insulin should be in the form of a dry powder which dissolves rapidly in aqueous solution.

The substance which enhances the absorption of insulin in the lung, hereinafter referred to as the enhancer, can be any of a number of compounds which act to enhance absorption through the layer of epithelial cells in the lower respiratory tract, and into the adjacent pulmonary vasculature. The enhancer can accomplish this by any of several possible mechanisms:

(1) Enhancement of the paracellular permeability of insulin by inducing structural changes in the tight junctions between the epithelial cells.

(2) Enhancement of the transcellular permeability of insulin by interacting with or extracting protein or lipid constituents of the membrane, and thereby perturbing the membrane's integrity.

(3) Interaction between enhancer and insulin which increases the solubility of insulin in aqueous solution. This may occur by preventing formation of insulin aggregates (dimers, trimers, hexamers), or by solubilizing insulin molecules in enhancer micelles.

(4) Decreasing the viscosity of, or dissolving, the mucus barrier lining the alveoli and passages of the lung, thereby exposing the epithelial surface for direct absorption of the insulin.

Enhancers may function by only a single mechanism set forth above, or by two or more. An enhancer which acts by several mechanisms is more likely to promote efficient absorption of insulin than one which employs only one or two. For example, surfactants are a class of enhancers which are believed to act by all four mechanisms listed above. Surfactants are amphiphilic molecules having both a lipophilic and a hydrophilic moiety, with varying balance between these two characteristics. If the molecule is very lipophilic, the low solubility of the substance in water may limit its usefulness. If the hydrophilic part overwhelmingly dominates, however, the surface active properties of the molecule may be minimal. To be effective, therefore, the surfactant must strike an appropriate balance between sufficient solubility and sufficient surface activity.

Another surfactant property that may be of importance is the net charge of the surfactant at the pH value in the lung (approximately 7.4). The isoelectric pH of insulin is 5.5. At pH 7.4, insulin has a negative net charge. This results in an electrostatic repulsion between insulin molecules, which in turn prevents aggregation and thereby increases the solubility. If the surfactant also is negatively charged, yet can interact with insulin by, for example, hydrophobic interactions, additional repulsion among the insulin molecules will occur. Therefore, an anionic surfactant will possess the additional advantage (compared to those having neutral or net positive charge at physiological pH) of enhancing absorption by helping stabilize insulin in the monomeric state.

A number of different compounds potentially useful as enhancers in the methods of the invention were tested in rats, as described in Example 5 below. Other substances with known absorption-enhancing properties, or with physical characteristics which make them likely candidates for use in the method of the invention, can be readily tested by one of ordinary skill in that in vivo assay, or alternatively in the in vitro assay described in Example 6.

It is possible that a combination of two or more enhancer substances also gives satisfactory results. The use of such a combination in the method of the invention is considered to be within the invention.

An enhancer useful in the methods of the invention will combine effective enhancement of insulin absorption with (1) lack of toxicity in the concentrations used and (2) good powder properties, i.e., lack of a sticky or waxy consistency in the solid state. Toxicity of a given substance can be tested by standard means, such as by the MTT assay, for example as described in Int. J. Pharm., 65 (1990), 249–259. The powder properties of a given substance may be ascertained from published data on the substance, or empirically.

One very promising type of enhancer is the salt of a fatty acid. It has been found that the sodium salts of saturated fatty acids of carbon chain length 10 (i.e., sodium caprate), 12 (sodium laurate) and 14 (sodium myristate) perform well in the method of the invention. The potassium and lysine salts of capric acid have also been found to be effective in the method of the invention. If the carbon chain length is shorter than about 10, the surface activity of the surfactant may be too low, and if the chain length is longer than about 14, decreased solubility of the fatty acid salt in water limits its usefulness.

Most preferably in the present invention the substance which enhances the absorption of insulin in the lower respiratory tract is sodium caprate.

In a particularly preferred embodiment therefore, this invention provides a therapeutic preparation comprising active compounds (A) insulin and (B) sodium caprate, in the form of a dry powder suitable for inhalation in which at least 50% of the total mass of active compounds (A) and (B) consists of (a) primary particles having a diameter of less than about 10 microns, for example between 0.01 and 10 microns and preferably between 1 and 6 microns, or (b) agglomerates of such particles; specifically, in this particularly preferred embodiment this invention provides:

a therapeutic preparation of insulin and sodium caprate, which preparation is in the form of a dry powder suitable for inhalation of which at least 50% by mass consists of (a) particles having a diameter of less than about 10 microns or (b) agglomerates of said particles;

a therapeutic preparation comprising insulin, sodium caprate and a pharmaceutically acceptable carrier, which preparation is in the form of a dry powder suitable for inhalation of which at least 50% by mass consists of (a) particles having a diameter of less than about 10 microns, or (b) agglomerates of said particles; and a therapeutic preparation comprising active compounds (A) insulin and (B) sodium caprate, wherein at least 50% of the total mass of active compounds (A) and (B) consists of particles having a diameter of less than about 10 microns, and a pharmaceutically acceptable carrier, which preparation is in the form of a dry powder preparation suitable for inhalation in which an ordered mixture may be formed between the active compounds and the pharmaceutically acceptable carrier.

Different counterions may change the solubility of the saturated fatty acid salt in water, such that an enhancer having a carbon length other than 10–14 would prove even more advantageous than the enhancers specifically mentioned hereinabove. Salts of unsaturated fatty acids may also be useful in the present invention since they are more water soluble than salts of saturated fatty acids, and can therefore have a longer chain length than the latter and still maintain the solubility necessary for a successful enhancer of insulin absorption.

Bile salts and bile salt derivatives were tested for usefulness as enhancers in the method of the present invention. All of those tested (sodium salts of ursodeoxycholate, taurocholate, glycocholate, and taurodihydrofusidate) effectively enhance insulin absorption in the lung.

Phospholipids were also tested as enhancers. It was found that a single-chain phospholipid (lysophospatidylcholine) was an effective enhancer, while two double-chain phospholipids (dioctanoylphosphatidylcholine and didecanoylphosphatidylcholine) were not. This may be explained by the fact that the double-chain phospholipids are much less soluble in water than their single-chain counterparts; however, it is reasonable to expect that double-chain phospholipids of shorter chain length, having greater water-solublility than their longer chain counterparts, will be of use as enhancers in the present invention so that both single- and double-chain phospholipids may be used.

One glycoside, octylglucopyranoside, was tested as an enhancer in the present invention and was found to have some absorption enhancing properties. Other alkyl glycosides such as thioglucopyranosides and maltopyranosides would also be expected to exhibit absorption enhancing properties in the methods of the present invention.

The cyclodextrins and derivatives thereof effectively enhance the nasal absorption of insulin, and may function similarly in the lung. Dimethyl-$\beta$-cyclodextrin has been tested in the method of the present invention and has been found to have an absorption enhancing effect.

Other potentially useful surfactants are sodium salicylate, sodium 5-methoxysalicylate, and the naturally occurring surfactants such as salts of glycyrrhizine acid, saponin glycosides and acyl carnitines.

For ionic enhancers (e.g., the anionic surfactants described above), the nature of the counterion may be important. The particular counterion selected may influence the powder properties, solubility, stability, hygroscopicity, and local/systemic toxicity of the enhancer or of any formulation containing the enhancer. It may also affect the stability and/or solubility of the insulin with which it is combined. In general, it is expected that monovalent metallic cations such as sodium, potassium, lithium, rubidium, and cesium will be useful as counterions for anionic enhancers. Ammonia and organic amines form another class of cations that is expected to be appropriate for use with anionic enhancers having a carboxylic acid moiety. Examples of such organic amines include ethanolamine, diethanolamine, triethanolamine, 2-amino-2-methylethylamine, betaines, ethylenediamine, N,N-dibensylethylenetetraamine, arginine, hexamethylenetetraamine, histidine, N-methylpiperidine, lysine, piperazine, spermidine, spermine and tris (hydroxymethyl)aminomethane.

Since effective enhancement of insulin absorption in the lung was observed for a number of the enhancers tested, it is expected that many more will be found which also function in this manner. Starch microspheres effectively enhance the bioavailability of insulin delivered via the nasal membranes and were tested as an enhancer in the methods of the invention. Although they proved to be of little use for delivery via the pulmonary route in the animal model utilized herein, it is thought that this was mainly due to technical difficulties which, if overcome, may lead to successful delivery via the pulmonary route. Chelators are a class of enhancers that are believed to act by binding calcium ions. Since calcium ions help maintain the dimensions of the space between cells and additionally reduce the solubility of insulin, binding of these ions would in theory both increase the solubility of insulin, and increase the paracellular permeability of insulin. Although one chelator tested, the sodium salt of ethylenediaminetetraacetic acid (EDTA), was found to be ineffective in enhancing absorption of insulin in the rat model tested, other calcium ion-binding chelating agents may prove to be more useful.

In general, it is desirable to keep the ratio of insulin to enhancer as high as possible, within the range that permits fast and efficient enhancement of insulin absorption. This is important in order to minimize the risk of adverse effects, both local and systemic, attributable to the enhancer. The optimal ratio of insulin to enhancer can be ascertained for any given enhancer by testing various proportions in in vivo models such as described herein. For example, insulin was combined with sodium caprate in the following w/w proportions: 50/50, 75/25, 82.5/17.5, and 90/10. Significant improvement in absorption of insulin was obtained with 50% and 25% sodium caprate; 10% gave poor improvement in absorption, and the results with 17.5% were intermediate. This indicates that the lowest effective concentration of sodium caprate for use in the methods of the invention is approximately 15–25%, and probably 20–25%. Other enhancers may have higher or lower optimal concentrations relative to insulin, and each individual enhancer must therefore be separately tested. Based upon the above results, however, it is expected that the optimal proportion of a surfactant type of enhancer will generally be between 10 and 50% of the insulin/enhancer mixture, for example between 15% and 50% such as between 25% and 50%. It should be noted that the above proportions represent the proportion of enhancer relative solely to insulin, and do not take into account any carrier or other additive which may be added, for example to improve the powder properties of the formulation.

The amount of insulin absorbed according to the present invention can be significantly higher than the amount absorbed in the absence of enhancer. In Example 4 herein it is shown that a therapeutic preparation according to the present invention, when inhaled, exhibits a bioavailability well over three times greater than that of an inhaled preparation of insulin alone.

Preferably the amount of insulin absorbed according to the present invention is significantly ($p<0.05$) higher than the amount absorbed in the absence of enhancer.

As stated hereinabove, additive substances commonly included in therapeutic preparations, such as pharmaceutically acceptable carriers, may be included in the theraputic preparation of the present invention. Additive substances may be included for example in order to dilute the powder to an amount which is suitable for delivery from the particular intended powder inhaler; to facilitate the processing of the preparation; to improve the powder properties of the preparation; to improve the stability of the preparation, e.g. by means of antioxidantia or pH-adjusting compounds; or to add a taste to the preparation. Any additive should not adversely affect the stability of the insulin or absorption enhancer, or disadvantageously interfere with the insulin absorption. It should also be stable, not hygroscopic, have good powder properties and have no adverse effects in the airways. As examples of potential additives may be mentioned mono-, di-, and polysaccharides, sugar alcohols and other polyols, such as for example lactose, glucose, raffinose, melezitose, lactitol, maltitol, trehalose, sucrose, mannitol and starch. As reducing sugars such as lactose and glucose have a tendency to form complexes with proteins, non-reducing sugars such as raffinose, melezitose, lactitol, maltitol, trehalose, sucrose, mannitol and starch may be preferred additives for use in the present invention. Depending upon the inhaler to be used, the total amount of such additives may vary over a very wide range. In some circumstances little or no additive would be required, whereas for example in the case of an inhaler requiring large powder volumes for operation, a very high percentage of the therapeutic preparation could consist of additive. The amount of additive desirable would be easily determined by a person skilled in the art according to particular circumstances.

A useful mechanism for delivery of the powder into the lungs of a patient is through a portable inhaler device suitable for dry powder inhalation. Many such devices, typically designed to deliver antiasthmatic or antiinflammatory agents into the respiratory system, are on the market. Preferably the device is a dry powder inhaler of a design which provides protection of the powder from moisture and has no risk from occasional large doses; in addition as many as possible of the following are desired: protection of the powder from light; high respirable fraction and high lung deposition in a broad flow rate interval; low deviation of dose and respirable fraction; low retention of powder in the mouthpiece; low adsorption to the inhaler surfaces; flexibility in dose size; and low inhalation resistance. The inhaler is preferably a single dose inhaler although a multi dose inhaler, preferably such as a multi dose, breath actuated, dry powder inhaler for multiple use, may also be employed. Preferably the inhaler used is a unit dose, breath actuated, dry powder inhaler for single use.

The described powder preparation can be manufactured in several ways, using conventional techniques. It may be necessary to micronize the active compounds and if appropriate (i.e where an ordered mixture is not intended) any carrier in a suitable mill, for example in a jet mill at some point in the process, in order to produce primary particles in a size range appropriate for maximal deposition in the lower respiratory tract (i.e., under 10 μm). For example, one can dry mix insulin and enhancer powders, and carrier where appropriate, and then micronize the substances together; alternatively, the substances can be micronized separately, and then mixed. Where the compounds to be mixed have different physical properties such as hardness and brittleness, resistance to micronisation varies and they may require different pressures to be broken down to suitable particle sizes. When micronised together, therefore, the obtained particle size of one of the components may be unsatisfactory. In such case it would be advantageous to micronise the different components separately and then mix them.

It is also possible first to dissolve the components including, where an ordered mixture is not intended, any carrier in a suitable solvent, e.g. water, to obtain mixing on the molecular level. This procedure also makes it possible to adjust the pH-value to a desired level. It is known that the nasal absorption of insulin is affected by the pH-value of the preparation, with increasing absorption when moving either up or down from the isoelectric point of insulin, which is around 5.5. However, the insulin may be less stable at pH significantly above or below 5.5, and furthermore the pharmaceutically accepted limits of pH 3.0 to 8.5 for inhalation products must be taken into account, since products with a pH outside these limits may induce irritation and constriction of the airways. To obtain a powder, the solvent must be removed by a process which retains the insulin's biological activity. Suitable drying methods include vacuum concentration, open drying, spray drying, and freeze drying. Temperatures over 40° C. for more than a few minutes should generally be avoided, as some degradation of the insulin may occur. Following the drying step, the solid material can, if necessary, be ground to obtain a coarse powder, then, if necessary, micronized.

If desired, the micronized powder can be processed to improve the flow properties, e.g., by dry granulation to form spherical agglomerates with superior handling characteristics, before it is incorporated into the intended inhaler device. In such a case, the device would be configured to ensure that the agglomerates are substantially deagglomerated prior to exiting the device, so that the particles entering the respiratory tract of the patient are largely within the desired size range.

Where an ordered mixture is desired, the active compound may be processed, for example by micronisation, in order to obtain, if desired, particles within a particular size range. The carrier may also be processed, for example to obtain a desired size and desirable surface properties, such as a particular surface to weight ratio, or a certain ruggedness, and to ensure optimal adhesion forces in the ordered mixture. Such physical requirements of an ordered mixture are well known, as are the various means of obtaining an ordered mixture which fulfills the said requirements, and may be determined easily by the skilled person according to the particular circumstances.

The invention will now be described by way of Examples, which are intended to illustrate but not limit the scope of the invention.

EXAMPLES

Comparative Example

Therapeutic preparation of insulin, without enhancer

Semisynthetic human insulin (Diosynth, 0.8 g) and water (150 ml) were added to a beaker. The pH was lowered with 1M HCl to pH 3.4 and then raised with 1M NaOH to pH 7.4, in order to dissolve the insulin.

Lactose (commercially available, 9.2 g) was added and the pH again adjusted to pH 7.4. The solution was stirred until clear or weakly opalescent, and concentrated by evaporation, at a temperature of 37° C. over a period of about two days.

The obtained solid cake was crushed, and sieved through a 0.5 mm sieve, and the resultant powder micronised through a jet mill to particles with a diameter of about 2 microns.

Example 1

Therapeutic preparation of insulin and sodium caprate; ratio 75:25

Semisynthetic human insulin (9.75 g) and water (250 ml) were added to a beaker. The pH was lowered with 1M HCl to pH 3.4 and then raised with 1M NaOH to pH 7.4, in order to dissolve the insulin.

Sodium caprate (Sigma, 3.25 g) was added and the pH again adjusted to pH 7.4. The solution was stirred until clear or weakly opalescent, and concentrated by evaporation, at a temperature of 37° C. over a period of about two days.

The obtained solid cake was crushed, and sieved through a 0.5 mm sieve, and the resultant powder micronised through a jet mill to particles of about 2 microns diameter.

Example 2

Therapeutic preparation of insulin and sodium caprate, with lactose; ratio 50:25:25

Semisynthetic human insulin (7.5 g) was dissolved in water (150 ml) as in Example 1. Sodium caprate (3.75 g) and lactose (3.75 g) were added and the procedure of Example 1 followed to produce a powder largely consisting of particles with a diameter of about 2 microns.

Example 3

Therapeutic preparation of insulin and sodium caprate, with lactose; ratio 4:4:92

The procedure of Example 2 was followed, using 0.5 g of semisynthetic human insulin, 150 ml water, 0.5 g sodium caprate and 11.5 g lactose.

Inhalation Studies

Study 1

The preparation of Example 1 was used in an inhalation study in two dogs. The preparation was filled into a Wright Dust Feed inhalation apparatus and administered to the dogs. The dosage level was 1 U./kg (1 U.=one unit of human insulin=35 µg human insulin, 100%) Blood glucose and plasma insulin values were measured at various time intervals and the results are summarised in Tables 1 and 2 below.

TABLE I

| Blood sample time after end of expo (minutes | Blood glucose (mmol/L) | Insulin conc (µU/ml) |
| --- | --- | --- |
| before | 3.9 | 6.70 |
| 0.5 | 3.6 | 120.66 |
| 5 | 2.8 | 194.47 |
| 10 | 2.6 | 195.39 |
| 20 | n.d | 139.74 |
| 22.5 | 1.6 | n.d |
| 31 | 2.0 | 73.42 |
| 45 | 1.7 | 47.49 |
| 59.5 | 1.7 | 36.21 |
| 89.5 | 2.3 | 19.28 |
| 120 | 3.0 | 14.58 |
| 240 | 4.5 | 5.28 | n.d. = not determined

TABLE II

| Blood sample time after end of expo (minutes) | Blood glucose (mmol/L) | Insulin conc (µU/ml) |
|---|---|---|
| before | 3.9 | 44.84 |
| 3 | 4.2 | 165.10 |
| 6 | 4.3 | 158.28 |
| 12 | 3.9 | n.d. |
| 14 | n.d. | 180.72 |
| 19 | 3.0 | 133.75 |
| 30 | 2.7 | 143.71 |
| 45 | 2.5 | 91.62 |
| 60 | 2.4 | 66.70 |
| 90 | 2.7 | 38.58 |
| 122 | 3.7 | 29.15 |
| 241 | 4.1 | n.d. |
| 242.5 | n.d. | 19.76 | n.d. = not determined

The tables illustrate that the insulin/sodium caprate formulation markedly increases the plasma level of insulin and decreases the blood glucose. The peak value for plasma insulin and the minimal value for blood glucose are reached after approximately 15 and 60 minutes, respectively.

Study 2

Figure 1:
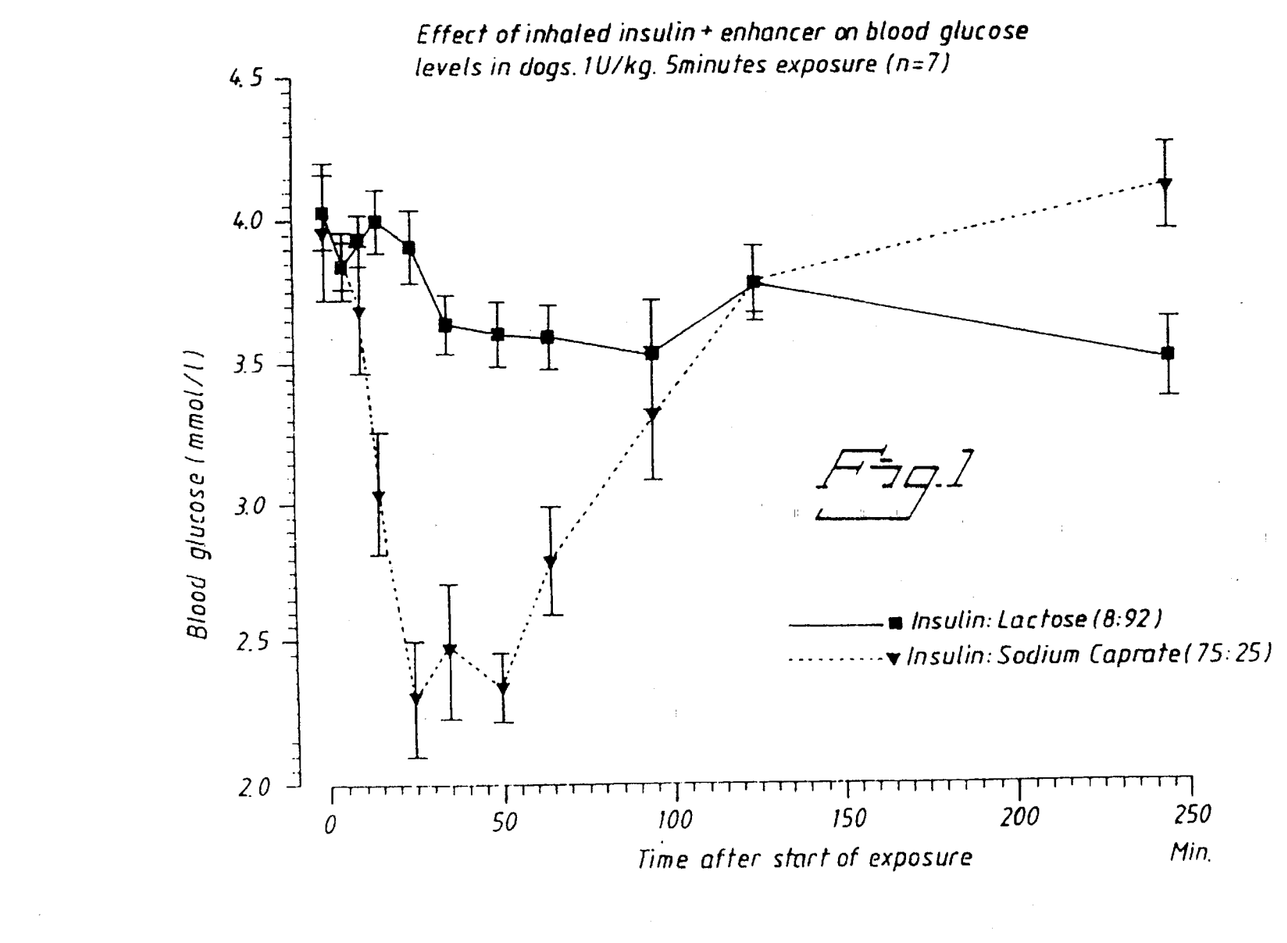
FIG. 1 is a graph comparing the effect of inhaled insulin plus enhancer to the effect of inhaled insulin without enhancer in blood glucose levels in a dog.
Figure 2:
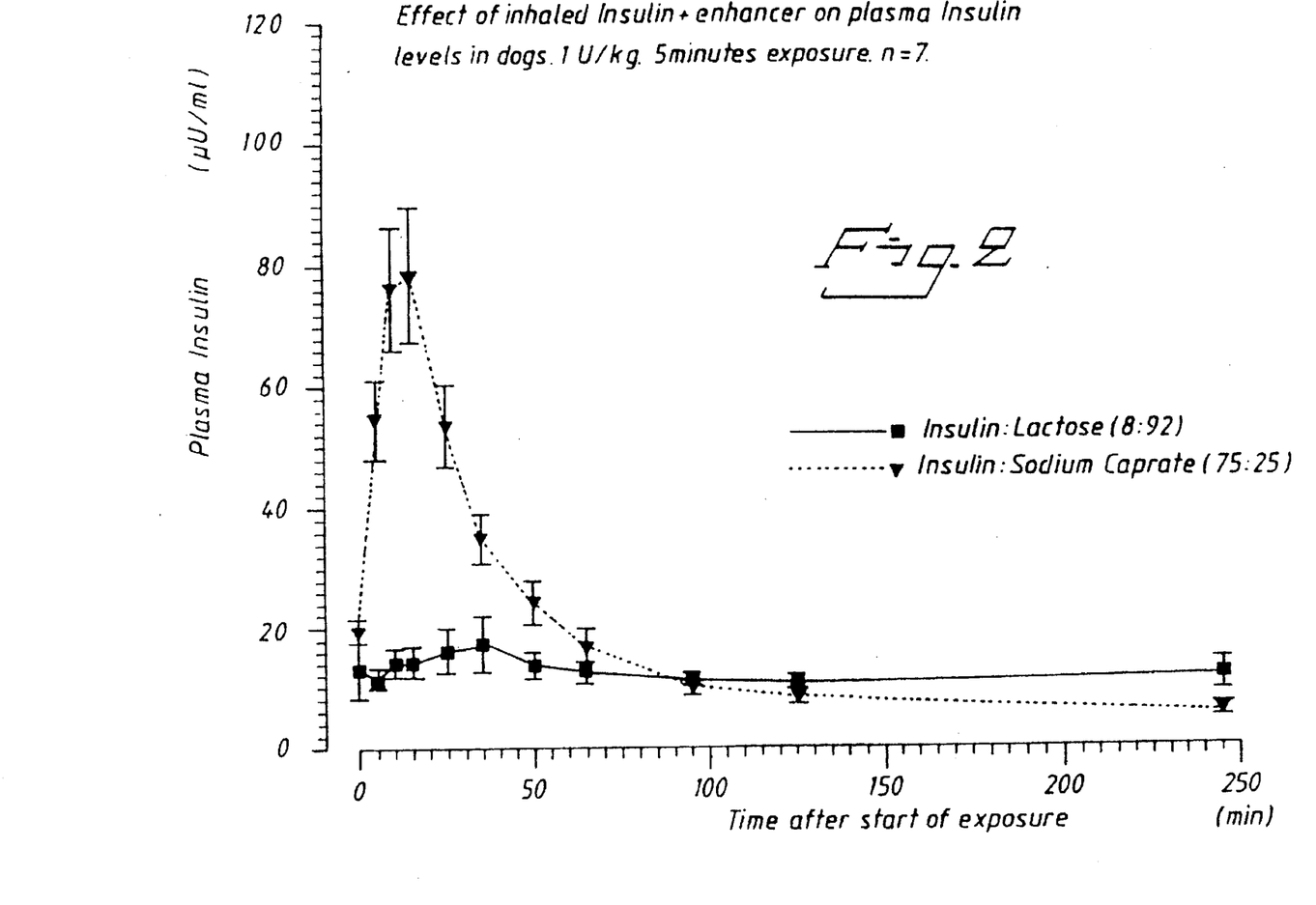
FIG. 2 is a graph comparing the effect of inhaled insulin plus enhancer to the effect of inhaled insulin without enhancer on blood glucose levels in a second dog.
Figure 3:
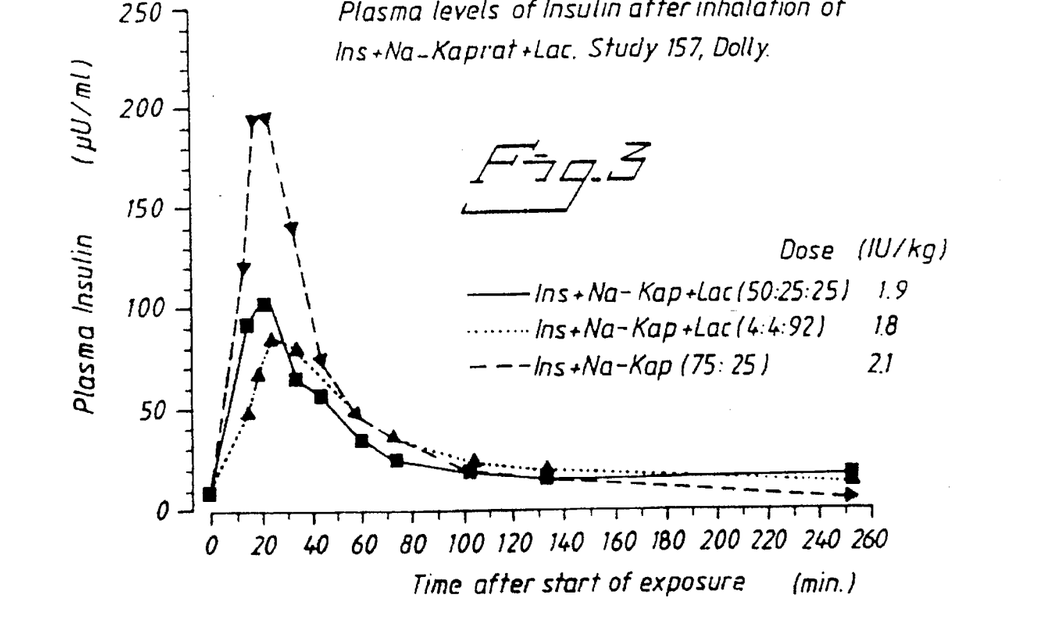
FIG. 3 is a graph comparing plasma levels of insulin after inhalation of three different formulations of insulin and enhancer in a dog.
Figure 4:
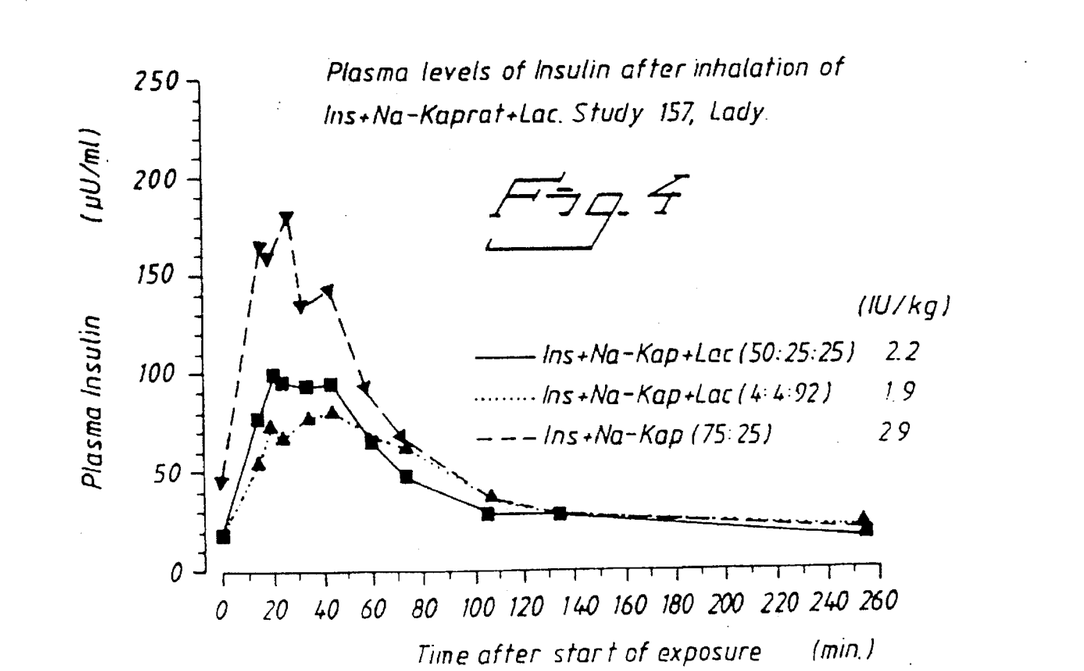
FIG. 4 is a graph comparing plasma levels of insulin after inhalation of three different formulations of insulin and enhancer in a second dog.
Figure 5:
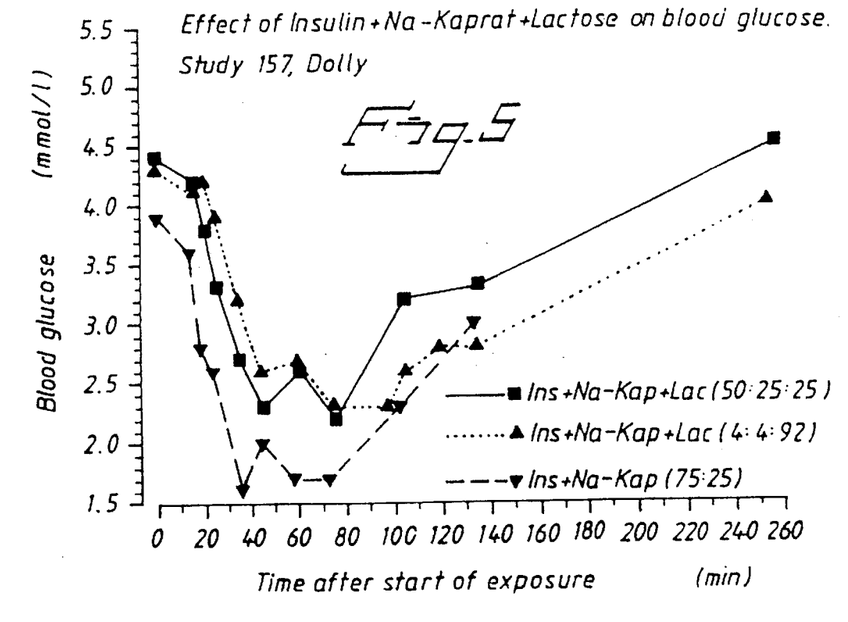
FIG. 5 is a graph comparing blood glucose levels following inhalation of three different formulations of insulin and enhancer in a dog.
Figure 6:
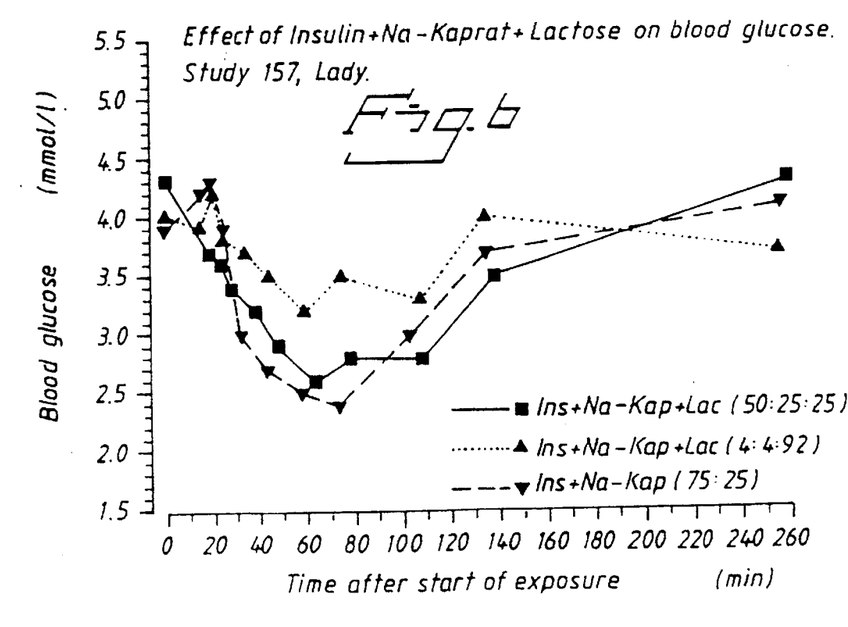
FIG. 6 is a graph comparing blood glucose levels following inhalation of three different formulations of insulin and enhancer in a second dog.
Figure 7:
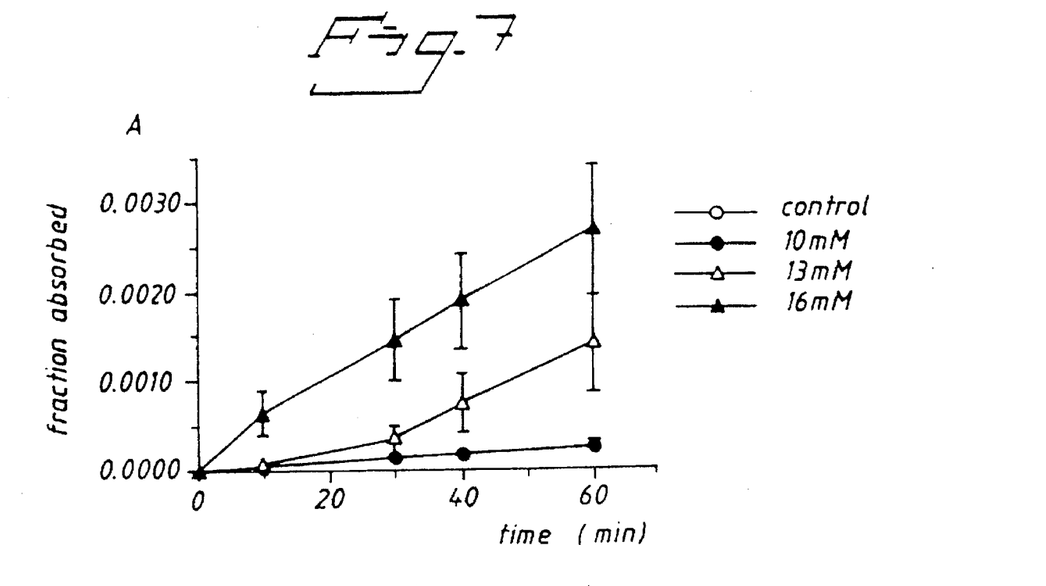
FIG. 7 is a graph showing the effect of three different concentrations of enhancer on transport of mannitol across a Caco-2 cell monolayer.
Figure 8:
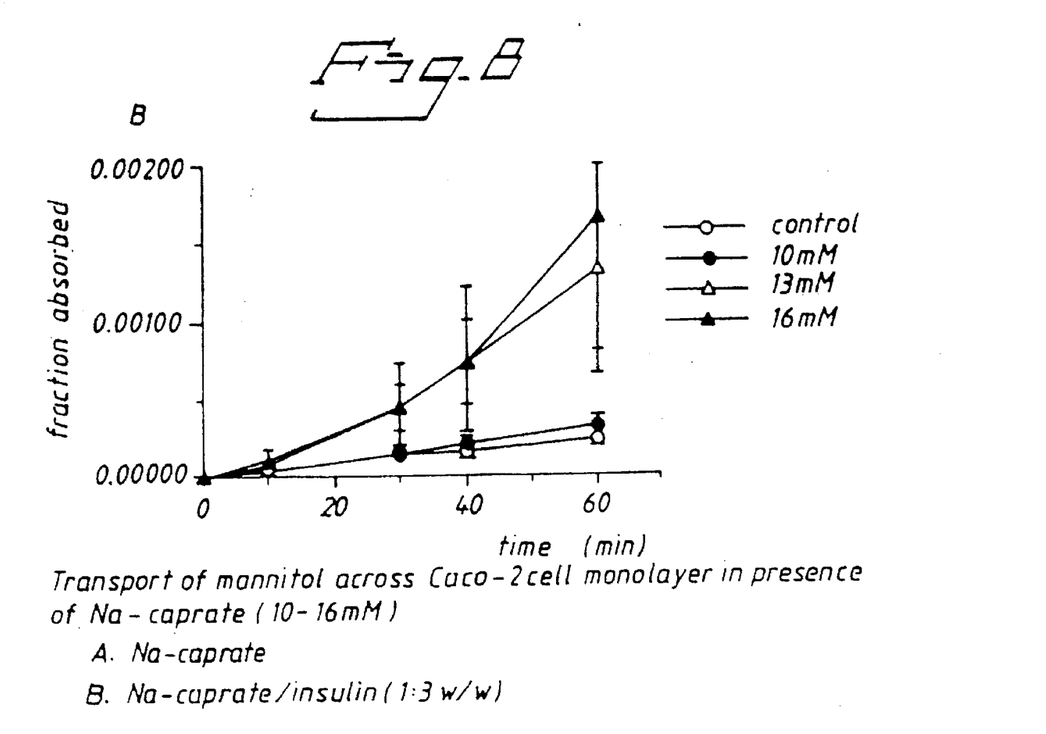
FIG. 8 is a graph showing the effect of three different concentrations of enhancer on transport of mannitol across a Caco-2 cell monolayer, in the presence of insulin.
Figure 9:
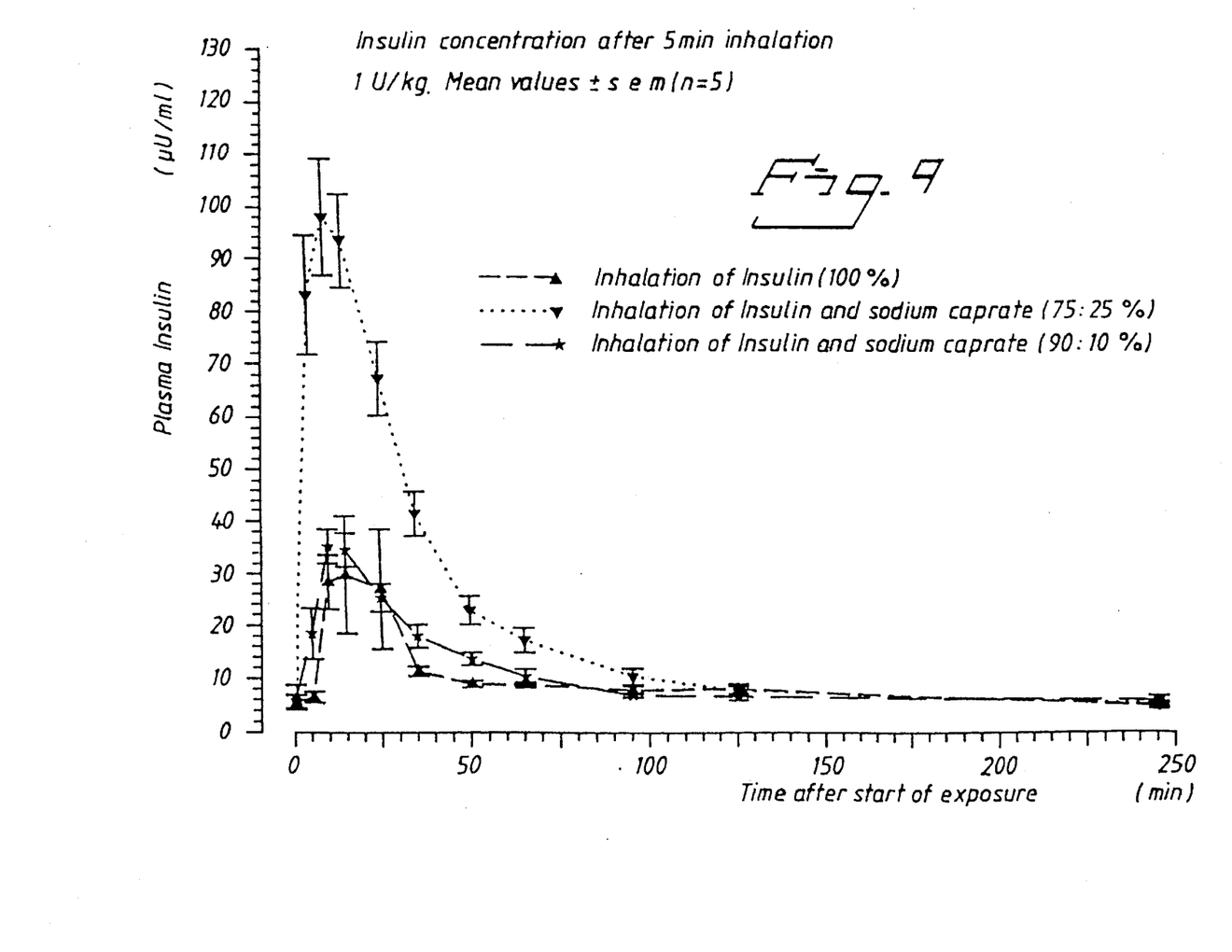
FIG. 9 is a graph comparing plasma insulin levels following inhalation of insulin alone, or insulin:sodium caprate 75:25 or 90:10.

The preparations of the Comparative Example and Example 1 were each administered to four or five dogs, by means of a Wright Dust Feed inhalation apparatus, at a constant dosage level of 1 U./kg. The effect of each formulation on plasma insulin levels and blood glucose levels was determined at various time points and the results are illustrated in FIGS. 1 and 2. It was found that, while the control formulation containing no enhancer produced essentially no change in plasma insulin levels, the formulation containing both insulin and enhancer produced a rise in plasma insulin levels from about 20 µU/ml at time zero to about 80 µU/ml 15 min. after inhalation of the powder. Likewise, the control animals registered a maximal drop in blood glucose of about 0.5 mmol/l following inhalation of insulin without enhancer, while the animals which inhaled insulin plus enhancer registered a transient drop of about 1.7 mmol/l, from about 4.0 mmol/l to about 2.3 mmol/l. Thus, insulin combined with the enhancer, sodium caprate, was quickly absorbed into and cleared from the systemic circulation, with a corresponding transient decrease in blood glucose levels. In contrast, insulin with carrier (lactose) but no enhancer was detectably absorbed only to a very small degree. ($p=0.0002$ for insulin/caprate vs. insulin/lactose.)

Study 3

The preparations of Examples 1–3 were each tested at varying dosage levels in two dogs. Administration of the preparations was by means of a Wright Dust Feed inhalation apparatus. Plasma insulin and blood glucose levels were measured at various time intervals following inhalation. The results are indicated in FIGS. 3–6, and show that insulin combined with sodium caprate in various proportions absorbs quickly, and that peak values are obtained after 20–30 minutes, followed by corresponding decreases in blood glucose levels. The results also indicate that by inhalation of insulin powder a plasma profile can be obtained which is more like the natural physiological profile than the profile obtained after subcutaneous injection of insulin.

Example 4

Insulin and sodium caprate, 75:25; mixing of micronised powders

Biosynthetic human insulin (53 g) was micronised in an Airfilco Jet Mill (Trade Mark, Airfilco Process Plant Limited), with pressurised nitrogen (feed pressure 7 bar, chamber pressure 5 bar), to a mass median diameter of 2.4 micrometers.

Sodium caprate (170 g) was micronised in an Airfilco Jet Mill (TM), with pressurised nitrogen (feed pressure 5 bar, chamber pressure 3 bar), to a mass median diameter of 1.6 micrometers.

The micronised biosynthetic human insulin (45 g) and sodium caprate (14.26 g) were dry mixed according to the following procedure: Half of the insulin was added to a mixing device comprising a mixing cylinder of volume 4.4 liters divided, by a sieve of width 1 mm, into two compartments, with a metal ring in each compartment to aid mixing and stirring. The sodium caprate and finally the rest of the insulin, were added. The mixing cylinder was closed, turned 180 degrees, and mounted in a motorised shaking apparatus. The motor was turned on and shaking continued for approximately two minutes, until all the insulin and sodium caprate had passed through the sieve. The motor was turned off and the mixing cylinder turned 180 degrees, again mounted on the shaking apparatus and shaking was again effected until all the powder had passed through the sieve. This procedure was repeated a further eight times to give a total mixing time of approximately 20 minutes.

The preparation so obtained was administered to 5 dogs by inhalation, using a Wright Dust Feed inhalation apparatus, at a dosage level of 1 U./kg, and the plasma insulin level determined at various time points after administration.

The results obtained were compared with the plasma insulin levels obtained when biosynthetic insulin, micronised as above to a mass median diameter of 2.4 micrometers, were administered to five dogs in the same way and at the same dosage levels, and with the plasma insulin levels obtained when a therapeutic preparation of insulin and sodium caprate in a ratio of 90:10 was administered to five dogs in the same way and at the same dosage levels as above. In this case the therapeutic preparation was prepared as follows: Human semisynthetic insulin was gel filtrated to reduce the zinc content from 0.52% to 0.01% relative to content of insulin. Insulin (4.5 g) and sodium caprate (0.5 g) were dissolved in water (232 ml). The solution was stirred until clear and the pH adjusted to 7.0. The solution was concentrated by evaporation at 37° C. over a period of about two days. The obtained solid cake was crushed, and sieved through a 0.5 mm sieve, and the resultant powder micronised through a jet mill to particles with a mass median diameter of 3.1 micrometers.

The results of these comparisons are presented in FIG. 9. The results demonstrate some improvement in the bioavailability of insulin with the 90:10 formulation, and a dramatic improvement in the bioavailability of insulin with the 75:25 preparation according to the present invention, as compared to insulin alone. ($p=0.0147$ for the difference between 75:25 and 100:0)

Example 5

Selection of enhancers

Each of the compounds listed in Table III was tested for its ability to enhance uptake of insulin, and thus affect blood glucose levels, in a rat model. Various forms of insulin were employed: recombinant or semisynthetic human or bovine. Each formulation was prepared as in Examples 1–3 above, drying and processing the insulin/enhancer solution to produce an inhalable powder.

The powder was administered to rats by inhalation, and the blood glucose levels of the rats were subsequently monitored. These levels were compared to the corresponding values obtained from rats which had inhaled insulin formulations without enhancer.

TABLE III

| Substance | Enhancer:Insulin:lactose | Effect |
|---|---|---|
| Octylglucopyranoside | 4:4:92 | (+) |
| Sodium ursodeoxycholate | 4:4:92 | + |
| Sodium taurocholate | 4:4:92 | + |
| Sodium glycocholate | 4:4:92 | + |
| Lysophosphatidylcholine | 4:4:92 | + |
| Dioctanoylphosphatidylcholine | 2:4:94 | (+) |
| Didecanoylphospatidylcholine | 4:4:94 | − |
| Sodium taurodihydrofusidate | 2:4:94 | + |
| Sodium caprylate | 25:75:0 | − |
| Sodium caprate | 10:90:0 | (+) |
| Sodium caprate | 17.5:82.5:0 | (+) |
| Sodium caprate | 25:75:0 | + |
| Sodium caprate | 4:4:92 | + |
| Sodium laurate | 25:75:0 | (+) |
| Potassium oleate | 4:4:92 | + |
| Potassium caprate | 27:73:0 | + |
| Lysine caprate | 35:65:0 | + |
| Sodium myristate | 30:70:0 | + |
| Dimethyl-β-cyclodextrin | 75:25:0 | + |

+ effect, i.e. enhancer gives a significant decrease in blood glucose level
− no or very small effect
(+) effect, not as marked as "+"

Example 6

Selection of enhancers

A standard in vitro assay utilizing an epithelial cell line, CaCo-2 (available through the American Type Culture Collection (ATCC), Rockville, Md., USA), has been developed to assess the ability of various enhancer compounds to promote transport of insulin and other markers across an epithelial cell monolayer, as a model for the epithelial cell layer which functions in the lung to separate the alveolus from the pulmonary blood supply. In this assay, the enhancer and insulin or other marker are dissolved in aqueous solution at various proportions and/or concentrations, and applied to the apical side of the cell monolayer. After 60 min incubation at 37° C. and 95% RH (relative humidity), the amount of the marker on the basolateral side of the cells is determined: for example, by use of a radioactively labelled marker. For the particular enhancer (sodium caprate) tested in the experiments shown in FIGS. 5 and 6, the amount of marker (mannitol, MW 360) which appears on the basolateral side is dependent upon the concentration of enhancer used, at least up to 16 mM sodium caprate (FIG. 7). This is true even when insulin is added to the enhancer/mannitol mixture (1:3 sodium caprate:insulin, by weight) (FIG. 8). This concentration of sodium caprate (16 mM) was also found to promote absorption of insulin across the cell monolayer. The amount of insulin which passed across the monolayer doubled in the presence of 16 mM sodium caprate, compared to the amount in the absence of any enhancer. It is expected that at higher concentrations of sodium caprate, the permeability of the cells will be further increased; however, the potential cytotoxicity of sodium caprate may prevent the use of substantially higher concentrations of this particular enhancer.

This in vitro model of epithelial cell permeability can be used as a screening tool for rapidly testing any desired enhancer for usefulness in the methods of the invention.

What is claimed is:

1. A process for the manufacture of a therapeutic composition comprising insulin, comprising forming, in a solvent, a solution of insulin and a substance which enhances the absorption of insulin in the lower respiratory tract;

removing the solvent to obtain a solid comprising said insulin and said substance; and processing said solid to obtain a powder of which at least 50% of the total mass consists of particles which have a diameter of up to 10 microns.

2. A process as claimed in claim 1, comprising adding to said solution, in addition to said substance which enhances the absorption of insulin in the lower respiratory tract, a pharmaceutically acceptable carrier.

3. A process for the manufacture of a therapeutic composition comprising insulin, comprising dry-mixing insulin together with a substance which enhances the absorption of insulin in the lower respiratory tract, and processing said mixture to obtain a powder of which at least 50% consists of particles which have a diameter of up to 10 microns.

4. A process as claimed in claim 3, further comprising dry-mixing a pharmaceutically acceptable carrier together with the insulin and the substance which enhances the absorption of insulin in the lower respiratory tract.

5. A process as claimed in claim 1, wherein the processing step comprises micronising the solid.

6. A process as claimed in claim 2, comprising the additional step of preparing an ordered mixture of said powder with a pharmaceutically acceptable carrier.

7. A process as claimed in claim 3, wherein the processing step comprises micronising the mixture.

8. A process as claimed in claim 4, comprising the additional step of preparing an ordered mixture of said powder with a pharmaceutically acceptable carrier.

9. A process as claimed in claim 1, characterised in that the weight ratio of said insulin to said substance in said powder is in the range 9:1 to 1:1.

10. A process as claimed in claim 3, characterised in that the weight ratio of said insulin to said substance in said powder is in the range 9:1 to 1:1.

11. A process as claimed in claim 1, characterised in that the insulin is semisynthetic or biosynthetic human insulin.

12. A process as claimed in claim 3, characterised in that the insulin is semisynthetic or biosynthetic human insulin.

13. A process as claimed in claim 1, characterised in that the substance is an anionic surfactant.

14. A process as claimed in claim 3, characterised in that said substance is an anionic surfactant.

15. A process as claimed in claim 1, characterised in that said substance is a salt of a fatty acid.

16. A process as claimed in claim 3, characterised in that said substance is a salt of a fatty acid.

17. A process as claimed in claim 15, characterised in that the fatty acid is capric acid.

18. A process as claimed in claim 16, characterised in that the fatty acid is capric acid.

19. A process as claimed in claim 1, characterised in that said substance is a bile salt.

20. A process as claimed in claim 3, characterised in that said substance is a bile salt.

21. A process as claimed in claim 19, characterised in that said bile salt is sodium taurocholate.

22. A process as claimed in claim 20, characterised in that said bile salt is sodium taurocholate.

23. A process as claimed in claim 1, characterised in that said substance is a phospholipid, alkyl glycoside, cyclodextrin, or cyclodextrin derivative.

24. A process as claimed in claim 3, characterised in that said substance is a phospholipid, alkyl glycoside, cyclodextrin, or cyclodextrin derivative.

25. A process as claimed in claim 2, characterised in that said carrier is selected from a monosaccharide, a disaccharide, a polysaccharide, and a sugar alcohol.

26. A process as claimed in claim 4, characterised in that said carrier is selected from a monosaccharide, a disaccharide, a polysaccharide, and a sugar alcohol.

27. A process as claimed in claim 2, characterized in that said carrier is selected from raffinose, melezitose, lactitol, maltitol, trehalose, sucrose, mannitol, and starch.

28. A process as claimed in claim 4, characterized in that said carrier is selected from raffinose, melezitose, lactitol, maltitol, trehalose, sucrose, mannitol, and starch.

29. A process as claimed in claim 1, characterized in that said substance is a salt of ursodeoxycholate or glycocholate.

30. A process as claimed in claim 3, characterized in that said substance is a salt of ursodeoxycholate or glycocholate.

31. A process as claimed in claim 1, characterized in that said substance is a salt of taurocholate.

32. A process as claimed in claim 3, characterized in that said substance is a salt of taurocholate.

* * * * *

UNITED STATES PATENT AND TRADEMARK OFFICE
CERTIFICATE OF CORRECTION

PATENT NO. : 5,658,878
DATED : August 19, 1997
INVENTOR(S) : Kjell Goran Erik Backstrom, Carl Magnus Olof Dahlback, Peter Edman and Ann Charlotte Birgit Johansson Page 1 of 1

It is certified that error appears in the above-identified patent and that said Letters Patent is hereby corrected as shown below:

On the Title Page, first column, at data number [30], line 2, replace "9400370" with --9400372--.

Signed and Sealed this

Third Day of July, 2001

Attest:

NICHOLAS P. GODICI
*Attesting Officer*  *Acting Director of the United States Patent and Trademark Office*

UNITED STATES PATENT AND TRADEMARK OFFICE
CERTIFICATE OF CORRECTION

PATENT NO.   : 5,658,878
DATED        : August 19, 1997
INVENTOR(S)  : Kjell G.E. Bäckström et al.

It is certified that error appears in the above-identified patent and that said Letters Patent is hereby corrected as shown below:

<u>Column 6,</u>
Line 34, replace "lysophospatidylcholine" with -- lysophosphatidylcholine --.
Line 35, replace "two" with -- one --.
Lines 35-36 and 38, replace "phospholipids" with -- phospholipid --.
Line 36, delete "dioctanoylphosphatidylcholine and".
Line 37, replace "were" with -- was --.
Line 39, replace "are" with -- is -- and replace "their" with -- its --.
Lines 39-40, replace "counterparts" with -- counterpart --.

Signed and Sealed this

Twenty-sixth Day of August, 2003

JAMES E. ROGAN
*Director of the United States Patent and Trademark Office*